United States Patent
Kagawa et al.

(10) Patent No.: US 7,682,602 B2
(45) Date of Patent: Mar. 23, 2010

(54) NEAR-INFRARED FLUORESCENT CONTRAST MEDIUM

(75) Inventors: Nobuaki Kagawa, Iruma (JP); Takeshi Habu, Hachioji (JP); Eiichi Ueda, Akishima (JP); Akihisa Nakajima, Sagamihara (JP)

(73) Assignee: Konica Minolta Medical & Graphic, Inc. (JP)

( * ) Notice: Subject to any disclaimer, the term of this patent is extended or adjusted under 35 U.S.C. 154(b) by 1442 days.

(21) Appl. No.: 11/011,806

(22) Filed: Dec. 14, 2004

(65) Prior Publication Data
US 2005/0136007 A1 Jun. 23, 2005

(30) Foreign Application Priority Data
Dec. 19, 2003 (JP) ............................. 2003-423282

(51) Int. Cl.
*A61B 10/00* (2006.01)
*A61K 5/00* (2006.01)
(52) U.S. Cl. .................... 424/9.6; 424/1.11; 424/1.65; 424/9.1
(58) Field of Classification Search ................ 424/1.11, 424/1.65, 9.1, 9.6; 546/1; 548/400
See application file for complete search history.

(56) References Cited

U.S. PATENT DOCUMENTS 6,083,485 A * 7/2000 Licha et al. .................. 424/9.6

FOREIGN PATENT DOCUMENTS

JP 2005-120026 A 5/2005

OTHER PUBLICATIONS

Supplementary European Search Report for Application No. 04807499.1-1211/1695960 PCT/JP2004019142 dated Jan. 30, 2009.

* cited by examiner

*Primary Examiner*—D L Jones
(74) *Attorney, Agent, or Firm*—Cantor Colburn LLP

(57) ABSTRACT

A near-infrared fluorescing contrast medium which exhibits superior imaging capability and is also difficult to accumulate in a living body, is disclosed, comprising a cyanine compound containing water-solubilizing groups and represented by the following formula. The imaging method by use thereof is also disclosed.

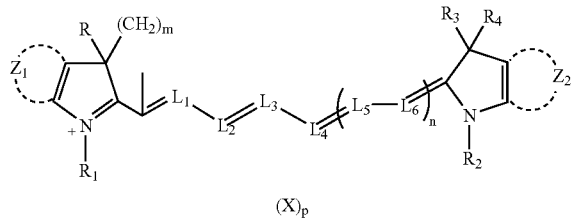

12 Claims, No Drawings

NEAR-INFRARED FLUORESCENT CONTRAST MEDIUM

FIELD OF THE INVENTION

The present invention relates to a near-infrared fluorescent contrast medium comprising a cyanine type compound and fluorescence contrast radiography by use of the contrast medium.

BACKGROUND OF THE INVENTION

In the initial stage of disease, to provide a suitable medical treatment for a disease, precise and prompt detection of morphological change of organ and tissue which has been caused in organism by the disease is desired through a simple method. Specifically in cases when treating cancer, it is essential for early treatment to specify the lesion region in the initial stage of carcinogenesis to definitely determine its size. Commonly known medical treatments for this purpose include, for example, living organ examination using an endoscope and imaging diagnosis such as radiography, MRI and sonography.

Living organ examination, whereby the lesion region can be directly observed, is effective for diagnostic definition; however, it is painful procedure for an examinee. Radiography or MRI exposes an examinee to radiation rays or a magnetic field potentially harmful to the human body, and when tracing the focus or lesion region with the elapse of time, the exposure time increases in proportion to the tracing time. In the measurement for MRI diagnosis, the photographing time is generally long and noises generated by the MRI photographing apparatus gives an examinee mental pressure. In addition, its facility and apparatus are large and require a large amount of labor and the cost for installation and operation is high.

On the other hand, light is a means capable of performing noninvasive diagnosis of organs using a relatively simple apparatus. There have been practically used, for example, a clinical thermometer in which the temperature of an infant is measured by detection of infrared rays emitted from the eardrum, a device for diagnosis for neonatal jaundice by numerical evaluation of the yellowing degree of bilirubin deposited onto subcutaneous tissue, a pulse oximeter for noninvasive measurement of aerated blood oxygen saturation ($SaO_2$) based on the degree of light absorption, and endoscopical observation of auto-fluorescence, employing the characteristic that auto-fluorescing of oncocyte is less than that of a normal cell (being excited at 450 nm and fluorescing at 520 nm). However, there is raised the problem that many hemoglobins exhibiting absorption in the visible region exist in organs and only information of the outermost surface of organ can be measured or collected.

In the near-infrared region at the wavelengths slightly longer than visible light, absorption of the respective substituents having a hydrogen bond occurs but such absorption is relatively small so that near-infrared rays are easily transmitted through tissue. It is contemplated that employing such characteristics of near-infrared rays make it feasible to measure bio-information without loading a useless load onto the body. However, light is strongly scattered by tissue so that it is generally not easy to know through which portion of the organ detected light has passed or from which portion information is transmitted. Recently, information of the deep portion of the body can also be obtained by combinations of a high-sensitive sensor, a laser generating extremely short pulses and simulation for internal light scattering employing Monte Carlo method.

There is noted fluorescent photography as a diagnostic method using near-infrared rays, in which near-infrared dyes are injected into a tumor portion to image the tumor portion. In this method, a compound capable, as a contrast medium, of fluorescing upon exposure to exciting light at wavelengths in the near-infrared region is dosed into a live body. Then, exciting light of near-infrared wavelengths is irradiated from outside the body and detection of emitted fluorescence from the fluorescent contrast medium concentrated at the tumor portion provides definite decision of the lesion portion.

There is known, as such a fluorescing contrast medium, indocyanine green which has been confirmed to be safe within a living body. It is said that veins in tumor portions are randomly open and close, causing retention of bloodstreams (so-call blood pool). When the indocyanine green is dosed to an animal exhibiting a tumor, the retention time of blood differs between the normal portion and the tumor portion (i.e., the indocyanine green is promptly discharged from the tissue comprised of normal cells), so that irradiation of exciting light at the wavelengths in the near-infrared region can cause the tumor portion to come out (Ohata et al., Basic Study of Cancer Diagnosis Using Indocyanine Green and Near-Infrared Topography in Rat Experiment Tumor, Nippon Ihokaishi, 62 (6), 284-286, 2002).

Since fluorescing contrast medium of cyanine type compounds was reported, there have been disclosed techniques using various peripheral cyanine type compounds as a contrast medium to achieve modification into a compound exhibiting enhanced hydrophilicity, molar absorption coefficient and quantum yield, as described in JP-A No. 2000-95758, 2002-526458, 2003-517025, 2003-160558 and 261464 (hereinafter, the term, JP-A refers to unexamined Japanese Patent Application Publication). In addition to resolving performance (imaging power) capable of discriminating lesion tissue from normal tissue, the medium needs to completely decomposed to be nontoxic or be completely discharged after imaging (non-accumulativeness). However, there has not been found any safer compound providing both of the foregoing or any other contrast medium containing the said compound.

SUMMARY OF THE INVENTION

Accordingly, it is an object of the present invention to provide a cyanine compound and a near-infrared fluorescent contrast medium containing a cyanine compound which not only exhibits superior imaging capability resulting in images with superior resolution which definitely discriminates lesion tissue from normal tissue but is also difficult to accumulate in a living body.

It is another object of the invention to provide an fluorescence imaging method using the fluorescent contrast medium and a diagnosis support method by the use thereof.

In one aspect the present invention is directed to a near-infrared fluorescent contrast medium comprising a cyanine compound represented by the following formula (I):

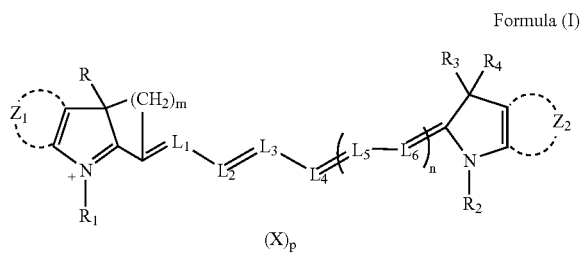

Formula (I)

wherein R is a hydrogen atom, a lower alkyl group or an aromatic group; $R_1$ and $R_2$, which may be the same or different, are each an aliphatic group substituted by a water-solubilizing group; $R_3$ and $R_4$, which may be the same or different, are each a lower alkyl group or an aromatic group, or $R_3$ and $R_4$ may combine with each other to form a carbocyclic ring; $L_1$ to $L_6$, which may be the same or different, are each a methine group, provided that when n is 1 or 2, $L_6$ may combine with $R_3$ or $R_4$ to form a carbocyclic ring and when n is 0, $L_4$ may combine with $R_3$ or $R_4$ to form a carbocyclic ring; $Z_1$ and $Z_2$, which may be same or different, are each a nonmetallic atom group necessary to form a 5- or 6-membered ring condensed with a 5-membered heterocyclic ring; X is a counter ion necessary to neutralize a charge of the molecule; p is the number of X necessary to neutralize a charge of the whole molecule; m is an integer of 2 to 4; and n is an integer of 0 to 2.

In another aspect the invention is directed to a fluorescence imaging process comprising the steps of introducing the foregoing near-infrared fluorescent contrast medium into a living body, irradiating exciting light onto the living body and detecting a near-infrared fluorescence emitted from the near-infrared fluorescent contrast medium.

DETAILED DESCRIPTION OF THE INVENTION

The cyanine compound of this invention emits fluorescence upon exposure to exciting light and the emitted near-infrared fluorescence is superior in transmission through organic tissue. Accordingly, a near-infrared fluorescent contrast medium containing the cyanine compound is superior in imaging ability resulting in resolution performance which can distinguish a lesion tissue from normal tissue, enabling to detect focus. In addition, the cyanine compound of this invention is water-soluble and easily discharged so that it can be used safely.

The cyanine compound of this invention and a near-infrared fluorescent contrast medium containing the cyanine compound will be further described in detail. The near-infrared fluorescent contrast medium means a contrast medium emitting fluorescence in the near-infrared region.

Cyanine Compound

The cyanine compound can be represented by formula (I):

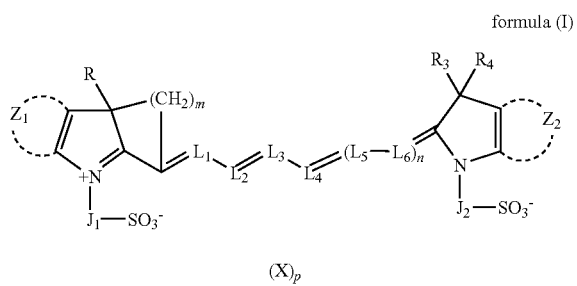

formula (I)

wherein R is a hydrogen atom, a lower alkyl group or an aromatic group; $R_1$ and $R_2$ which may be the same or different, are each an aliphatic group substituted by a water-solubilizing group; $R_3$ and $R_4$, which may be the same or different, are each a lower alkyl group or an aromatic group, or $R_3$ and $R_4$ may combine with each other to form a carbon-cyclic ring, or when n is 1 or 2, $L_6$ may combine with $R_3$ or $R_4$ to form a carbocyclic ring and when n is 0, $L_4$ may combine with $R_3$ or $R_4$ to form a carbocyclic ring.

$L_1$ to $L_6$, which may be the same or different, are each a methine group.

$Z_1$ and $Z_2$, which may be same or different, are each an atomic group necessary to form a 5- or 6-membered ring condensed with a 5-membered heterocyclic ring.

X is a counter ion necessary to neutralize a charge of the molecule, p is the number of X necessary to neutralize a charge of the whole molecule, and m is an integer of 2 to 4; and n is an integer of 0 to 2.

In the foregoing formula (I), R represents a hydrogen atom, a lower alkyl group or an aromatic group.

The lower alkyl group is a straight chain or branched alkyl group of 1 to 5 carbon atoms and specific examples thereof include methyl, ethyl, propyl, butyl and isobutyl. The groups may be substituted by a substituent and examples of such a substituted lower alkyl group include 2-hydroxyethyl, 3-sulfamoylpropyl and 3-carboxypropyl.

The aromatic group include a substituted or unsubstituted carbon aromatic ring group (or aromatic hydrocarbon group) and a heterocyclic aromatic group (or aromatic heterocycle group), and examples thereof include phenyl, m-hydroxyphenyl, p-methoxyphenyl, thienyl, pyridyl and pyrimidinyl.

In the formula (I), $R_1$ and $R_2$ may be the same with or different from each other, and represent an aliphatic group substituted by a water-solubilizing group. Examples of an aliphatic group include an alkyl group, an alkenyl group, a cyclic alkyl group and an alkynyl group.

The alkyl group preferably is a straight chain or branched lower alkyl group of 1 to 5 carbon atoms and specific examples thereof include methyl, ethyl, propyl, isopropyl, butyl, isobutyl, sec-butyl, tert-butyl, pentyl, isopentyl, neopentyl, 2-methylpropyl, and 1,1-dimethylpropyl. The alkenyl group preferably is a straight chain or branched lower alkenyl group of 3 to 5 carbon atoms and specific examples thereof include allyl, 2-butenyl and isobutenyl. The cyclic alkyl group preferably is a lower cyclic alkyl group of 3 to 6 carbon atoms, and specific examples thereof include cyclopentyl, cyclobutyl, cyclopentyl and cyclohexyl. The alkynyl preferably is a straight chain or branched lower alkenyl group of 3 to 5 carbon atoms, and specific examples thereof include 2-propynyl and 2-butynyl.

Examples of the water-solubilizing group include a carbamoyl group, sulfonic acid group, carboxyl group, hydroxy group and phosphoric acid group. Preferred examples of the aliphatic group substituted by a water-solubilizing group include 2-hydroxyethyl, 2-hydroxy-3-sulfopropyl, 3-hydroxypropyl, carboxymethyl, carboxymethyl, carboxybutyl, 2-phosphonoethyl, 3-phosphonopropyl, sulfomethyl, 2-sulfoethyl, 3-sulfopropyl, 4-sulfobutyl, 3-sulfobutyl and 2-hydroxy-3-sulfopropyl. Specifically, $R_1$ and $R_2$ each are more preferably a lower alkyl group substituted by a sulfonic acid group and having 1 to 5 carbon atoms, such as 2-sulfoethyl, 3-sulfopropyl, 4-sulfobutyl, 3-sulfobutyl and 2-hydroxy-3-sulfopropyl.

In the formula (I), $R_3$ and $R_4$, which may be the same or different, are each a lower alkyl group or an aromatic group. Examples of the lower alkyl group or aromatic group are the same as exemplified in the foregoing lower alkyl group or aromatic group. $R_3$ and $R_4$ may be non-metallic atom groups, that is, $R_3$ and $R_4$ may combine with each other to form a carbon-cyclic ring, or when n is 1 or 2, $L_6$ may combine with $R_3$ or $R_4$ to form a carbocyclic ring and when n is 0, $L_4$ may combine with $R_3$ or $R_4$ to form a carbocyclic ring.

Examples of a carbocyclic ring formed by the combination of $R_3$ and $R_4$ include a cyclopropane ring, cyclobutane ring, cyclopentane ring and cyclohexane ring. Examples of the carbocyclic ring formed by the combination of $L_6$ with $R_3$ or $R_4$ include a cyclobutene ring, cyclopentene ring and cyclohexane ring. These carbocyclic ring may be substituted by a substituent group, such as a substituted or unsubstituted lower alkyl group, sulfonic acid group, carboxyl group, hydroxy group, cyano group, amino group and substituted amino group [e.g., dimethylamino, ethyl-4-sulfobutylamino, di(3-sulfopropyl)amino]. The pyrrole ring bonded with nonmetallic atom group $Z_1$ forms a carbocyclic ring formed by the combination of $R_3$ or $R_4$ with $L_6$ or $L_4$. The formation of such a carbocyclic ring results in advantages that absorption at longer wavelengths is achieved without making the structure of the compound unstable or without introducing an unwanted hydrophobic conjugated structure which enhances affinity to tissue. Furthermore, introduction of such a carbocyclic ring is inert in living organism and contributes accomplishment of a compound exhibiting superior fluorescence characteristics.

In the formula (I), $Z_1$ and $Z_2$, which may be same or different, are each a nonmetallic atom group necessary to form a 5- or 6-membered ring condensed with a nitrogen-containing 5-membered heterocyclic ring. Rings formed by such a nonmetallic atom group include a 5-membered ring, a 6-membered ring, a condensed ring constituted by at least two cycles, a heterocyclic 5-mmembered ring, a heterocyclic 6-membered ring and a condensed heterocyclic ring constituted by at least two cycles. These rings may be substituted by a substituent at any position. Examples of such a substituent include a sulfonic acid group, a carboxyl group, hydroxy group, cyano group, amino group, substituted amino group (e.g., dimethylamino, ethyl-4-sulfobutylamino, di(3-sulfopropyl)amino) and a substituted or unsubstituted alkyl group attached directly or via a divalent linkage group to the ring. Preferred examples of such a divalent linkage groups include —O—, —NHCO—, —NHSO$_2$—, —NHCOO—, —NH-CONH—, —COO—, —CO— and —SO$_2$—. Examples of unsubstituted alkyl group attached directly or via a divalent linkage group to the ring include methyl, ethyl, propyl, and butyl, and preferably methyl and ethyl. The substituted alkyl group may be substituted at any position of the alkyl group and preferred substituents include a sulfonic acid group, carboxyl group and hydroxyl group, and of these, a sulfonic acid group is preferred.

Of the ring formed by the nonmetallic atom group indicated above, a carbocyclic or nitrogen-containing heterocyclic ring substituted a water-solubilizing group is specifically preferred.

In the formula (I), $L_1$ to $L_6$ are each a methine group, which may be the same or different, and the methine group may be substituted by a substituent. Examples of a substituent include unsubstituted or substituted alkyl group such as methyl, ethyl, propyl, butyl, pentyl, 2-phenoxyethyl or 2-sulfoethyl; a halogen atom such as chlorine, fluorine, bromine or iodine; unsubstituted or substituted aryl group such as a phenyl, phenyl substituted by a sulfonic acid group, phenyl substituted by a methoxy group or naphthyl; a heterocyclic group such as furyl, thienyl, pyrrolyl, imidazolyl, pyrrolidyl or morpholine; a lower alkoxy group such as methoxy or ethoxy; an amino group or substituted amino group such as dimethylamino or 2-sulfoethylamino. Of the foregoing substituents for the methine group represented by $L_1$ to $L_6$, an alkyl group, amino group and heterocyclic group are preferred.

Substituents for the methine groups of $L_1$ to $L_6$ may be combined with each other to form a ring containing three methine groups and the thus formed ring may further link with another ring containing methine group to form a condensed ring. Specific examples of a ring containing three methine groups, formed by the combination of substituents for the methine groups of $L_1$ to $L_6$ include a 4-oxo-2-hydroxycyclobutene ring, cyclopentene ring, cyclohexane ring and 4-dimethylcyclohexene ring. Of these, a cyclopentene ring is preferred in this invention.

In "pX" of the formula (I), X represents a counter ion necessary to neutralize a charge of the molecule and p represents the number of X(s), necessary to neutralize the whole charge of the molecule. The value of p is not specifically limited if the whole charge of the molecule can be neutralized, and is usually 1 to 10. The counter ion may be a cation or an anion, including anyone forming a nontoxic salt. Specific examples of a cation include an alkali metal ion such as sodium or potassium; an alkaline earth metal ion such as magnesium or calcium; ammonium or an organic ammonium ion such as triethylammonium, tributylammonium or pyridinium; an ammonium ion of an amino acid such as lysine salt or alginic acid salt. Specific examples of an anion include a halide ion such as chloride, bromide or iodide ion; sulfate ion; an organic carboxylic acid ion such as acetic acid or citric acid; and toluenesulfonate ion. Of the counter ions, sodium ion or chloride ion capable of reducing toxicity is specifically preferred.

Of compounds represented by the foregoing formula (I), a cyanine compound represented by the following formula (II) which contains at least two water-solubilizing groups in the molecule, is preferred:

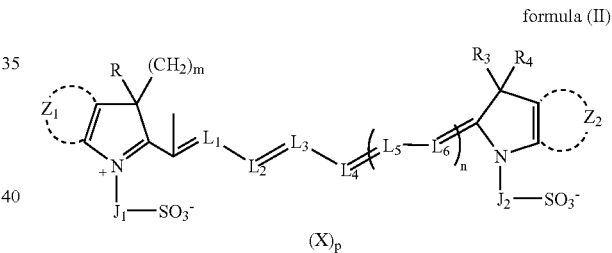

formula (II)

wherein $J_1$ and $J_2$, which may be the same or different, is an alkylene group having 1 to 5 carbon atoms; R, $R_3$, $R_4$, $L_1$ to $L_6$, $Z_1$, $Z_2$, m, n, p and X are each the same as defined in the foregoing formula (I).

Examples of the alkylene group having 1 to 5 carbon atoms, represented by $J_1$ and $J_2$ include methylene, ethylene, propylene, butylenes, pentylene and 2-methylpropylene, and of these, ethylene is preferred.

The compound represented by the foregoing formula (II) preferably a cyanine compound represented by the following formula (III):

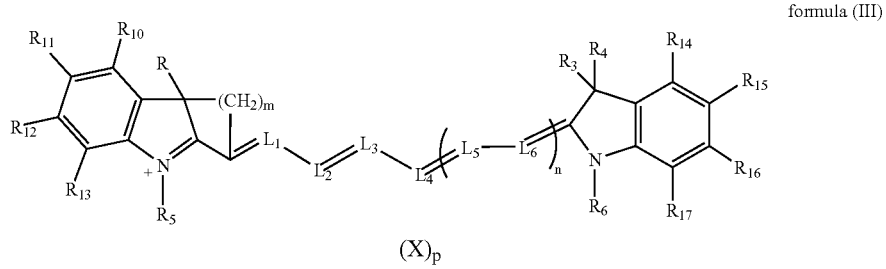

formula (III)

wherein $R_5$ and $R_6$ are each a sulfoalkyl group having 3 to 5 carbon atoms and substituted by water-solubilizing group; R, $R_3$, $R_4$, $L_1$ to $L_6$, m, n, p and X are each the same as defined in the foregoing formula (I); $R_{10}$ to $R_{17}$, which may be the same or different, are each a hydrogen atom or a substituent having a π value of not more than 0.3.

The foregoing $R_5$ and $R_6$ are each a sulfoalkyl group having 3 to 5 carbon atoms and substituted by a water-solubilizing group; examples of such a water-solubilizing group include the same one as defined in the formula (I) and a hydrophilic anionic group. Examples of the anionic group include a carbamoyl group, a sulfamoyl group, an acetoamide group, a sulfonamide group, and a methanesulfonamido group.

Specific examples of the sulfoalkyl group having 3 to 5 carbon atoms and substituted by a water-solubilizing group include 2-hydroxy-3-sulfopropyl, 2-carbamoylmethyl-4-sulfobutyl, 2-acetoamido-4-sulfobutyl, 2-sulfamoyl-3-sulfopropyl, 3-methanesulfonamido-5-sulfopentyl, 3-methanesulfonyl4-sulfobutyl, 2-carboxy-4-sulfobutyl and 3-phosphonooxy-5-sulfobutyl, and of these, 2-hydroxy-3-sulfopropyl is preferred.

In the formula (III), $R_{10}$ to $R_{17}$, which may be the same or different, is a hydrogen atom or a substituent exhibiting a π value of less than 0.3. Next, the π value used in the definition of $R_{10}$ to $R_{17}$ will be described.

The π value, which has been well established in the art, is a parameter indicating the influence of a substituent group on hydrophilicity/hydrophobicity (or lipophilicity) of a compound molecule and defined by the following equation:

$$\pi = \log P(PhX) - \log P(PhH)$$

wherein P is a partition coefficient of a compound with respect to octanol/water system, and the difference of a log P value (that is the logarithm of P) of a benzene containing a substituent group X (denoted as "PhX") from that of benzene (denoted as "PhH") is defined as the π value. Generally, the π value increases-with increasing hydrophobicity (of the ring substituent with hydrogen=zero).

The log P value can be determined by measurement based on the method described in the following literature (a), or by calculation using a fragment method described in literature (a) or a software package described in literature (b). In cases when the measure value and the calculated value are not coincide, the measured value is used as a π value:

(a) C. Hansch, A. J. Leo, "Substituent Constants for Correlation Analysis in Chemistry and Biology", John Wiley & Sons, New York, 1979;

(b) Medichem Software Package (3.54 edition, available from Pomona College, Claremont, Calif.).

The thus determined π values for the respective substituents are collected in the Tables of the foregoing literature (a). Typical substituents exhibiting a π value of less than 0.3 are extracted as follows:

| Substituent | value |
|---|---|
| $OSO_3H$ | −4.76 |
| OH | −0.67 |
| CN | −0.57 |
| $COCH_3$ | −0.55 |
| COOH | −0.32 |
| $OCCH_3$ | −0.02 |
| $COOCH_3$ | −0.01 |
| H | 0.00 |
| F | 0.14 |
| $N(CH_3)_2$ | 0.18 |

Preferred examples of a substituent exhibiting a π value of less than 0.3 include a phosphono group, sulfonic acid group, carboxyl group, hydroxyl group, cyano group, substituted amino group (e.g., dimethylamino, ethylamino), and substituted or unsubstituted methyl or ethyl group bonded to a ring via a linkage group of a π value of less than 0.3 and exhibiting a π value of less than 0.3. The linkage group of a π value of less than 0.3 is, for example, —O—, —NHCO—, —$NHSO_2$—, —NHCOO—, —NHCONH—, —COO—, —CO— or —$SO_2$—. Examples of a substituted or unsubstituted methyl or ethyl group exhibiting a π value of less than 0.3 include methoxy, 2-sulfoethyl, 2-hydroxyethyl, methylaminocarbonyl, methoxycarbonyl, acetyl, acetoamide, polopionylamino, ureido, methanesulfonylamino, ethanesulfonylamino, ethylaminocarbonyloxy, and methanesulfonyl groups. Of these substituent exhibiting a π value of less than 0.3, a sulfonic acid group is preferred.

The property specifically needed to use in vivo a cyanine compound as a contrast medium is being water-soluble. In the near-infrared fluorescent contrast medium of this invention, introduction of at least three sulfonic acid groups into the compound results in marked improvement in water-solubility of the compound. For the cyanine compound to be water-soluble, the number of sulfonic acid groups preferably is at least 4.

A sulfonic acid group is preferably introduced to the position of $R_1$, $R_2$, $Z_1$ and/or $Z_2$ of formula (I), to the position of $Z_1$ and/or $Z_2$ of formula (II), or to any position of $R_5$, $R_6$ and $R_{10}$ to $R_{17}$ of formula (III). The sulfonic acid group is also preferably introduced to $L_4$ of the conjugated methine chain via a divalent linkage group such as an alkylene group.

In the formulas (I), )II) and (III), m represents an integer of 2 to 4; and n represents an integer of 0 to 2 and n is preferably 1.

The cyanine compound relating to this invention is one represented by the formulas (I) to (III) and preferably contains at least three sulfonic acid groups in the molecule, and more preferably at least four sulfonic acid groups. Of the cyanine compounds of this invention is preferred a sodium salt of a compound represented by the formula (III) in which $R_5$ and $R_6$ are each a lower alkyl group having 3 to 5 carbon atoms and substituted by a nonionic water-solubilizing group and a sulfonic acid group, and at least three sulfonic acid groups are included in the molecule.

Specific example of the compounds represented by formula (I) [including those of formulas (II) and (III)] are shown below, but the invention is not limited to these.

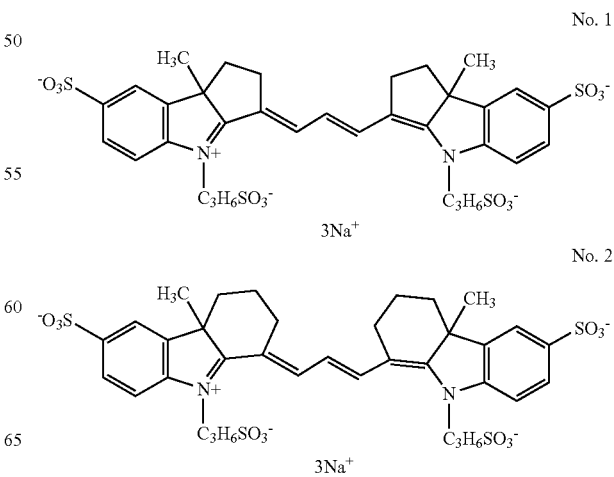

-continued
No. 3
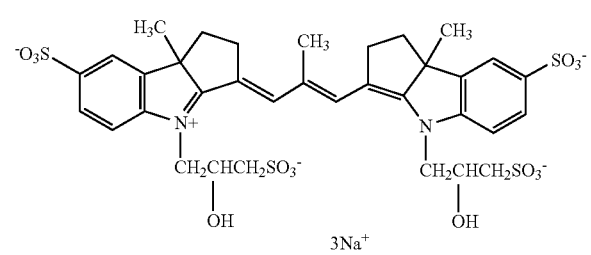
3Na⁺
No. 4
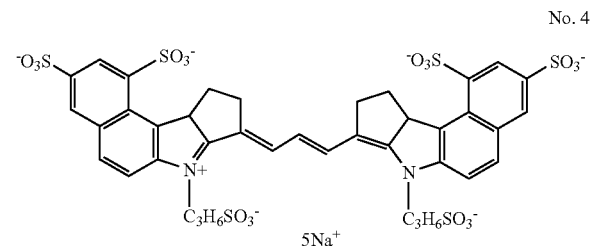
5Na⁺
No. 5
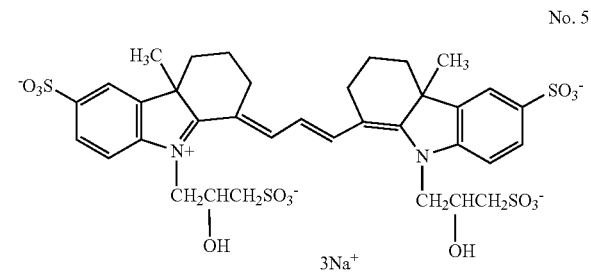
3Na⁺
No. 6
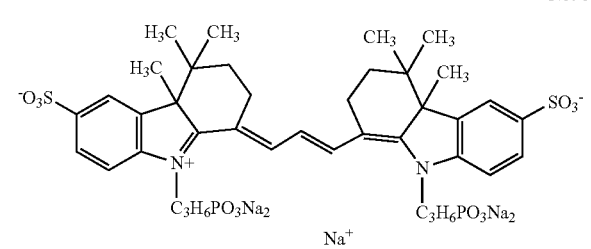
Na⁺
No. 7
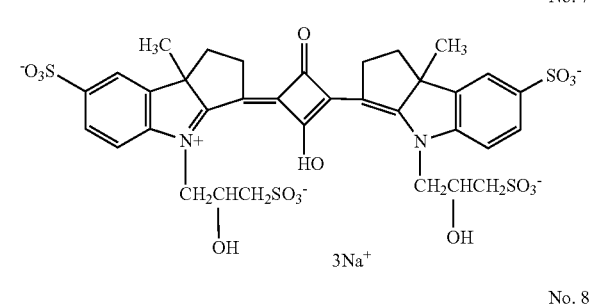
3Na⁺
No. 8
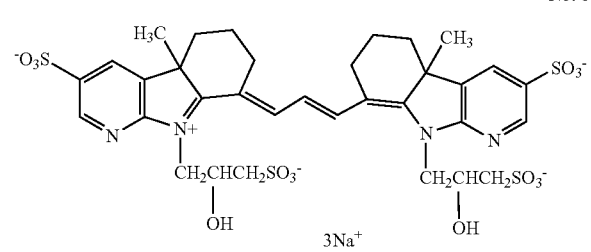
3Na⁺
-continued
No. 9
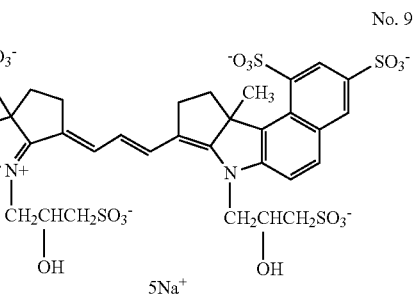
5Na⁺
No. 10
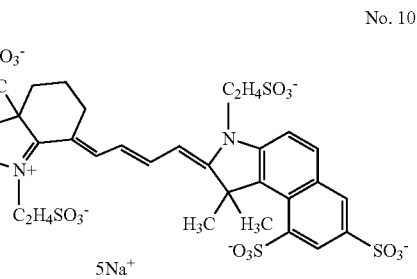
5Na⁺
No. 11
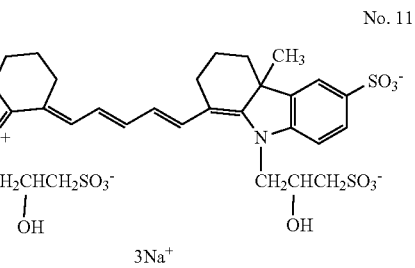
3Na⁺
No. 12
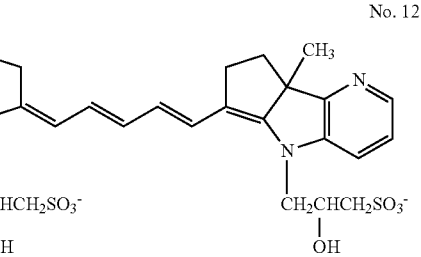
Na⁺
No. 13
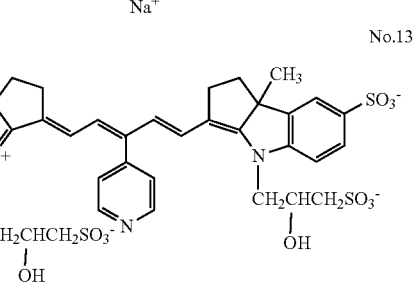
3Na⁺
No. 14
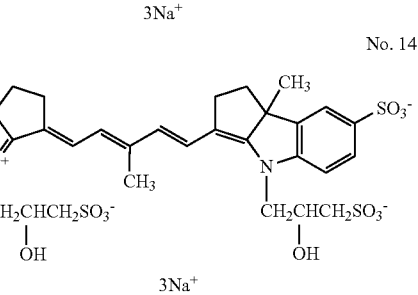
3Na⁺

-continued
No. 15
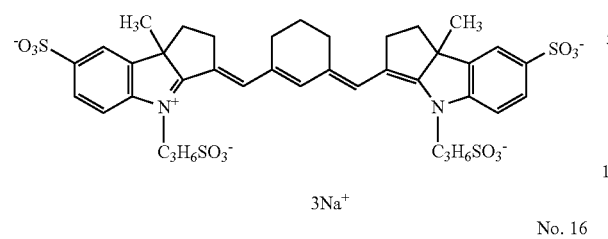
3Na+
No. 16
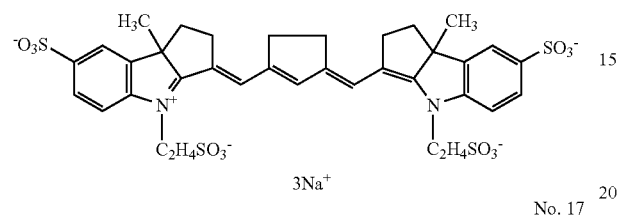
3Na+
No. 17
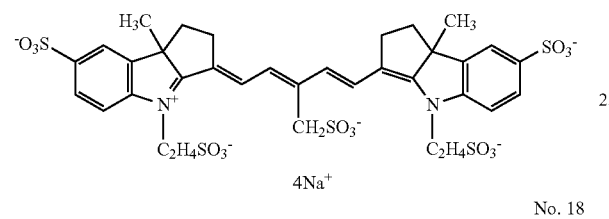
4Na+
No. 18
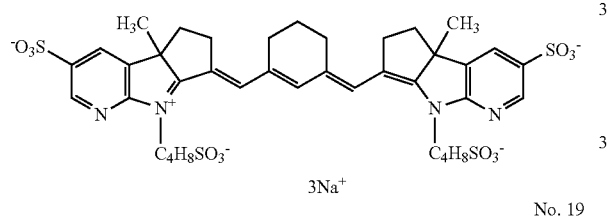
3Na+
No. 19
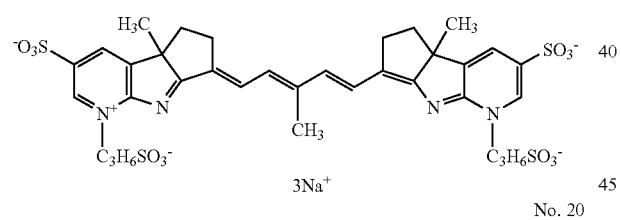
3Na+
No. 20
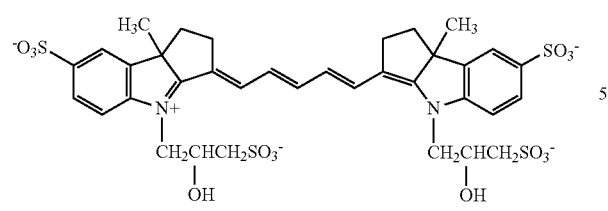
3Na+
No. 21
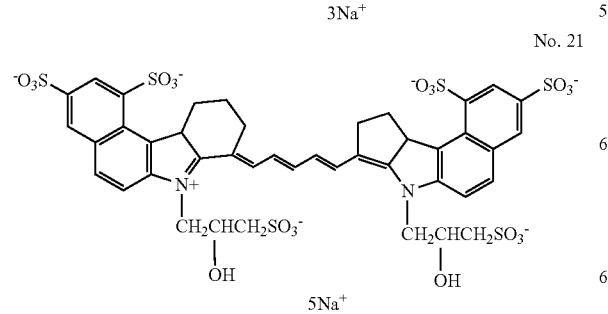
5Na+
-continued
No. 22
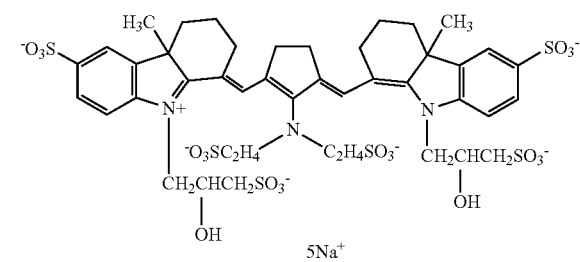
5Na+
No. 23
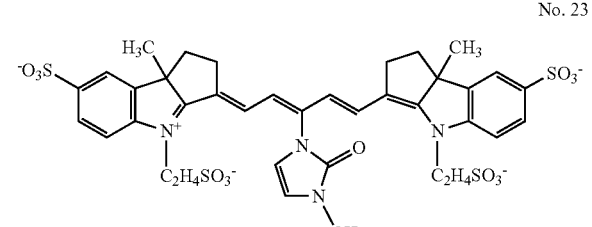
3Na+
No. 24
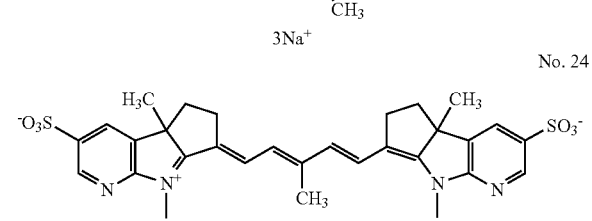
3Na+
No. 25
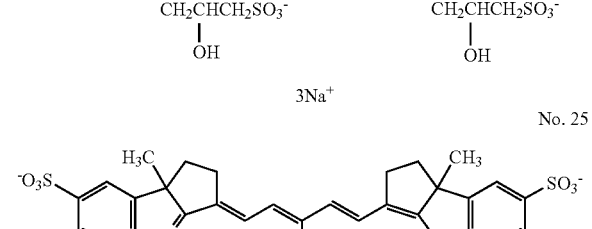
4Na+
No. 26
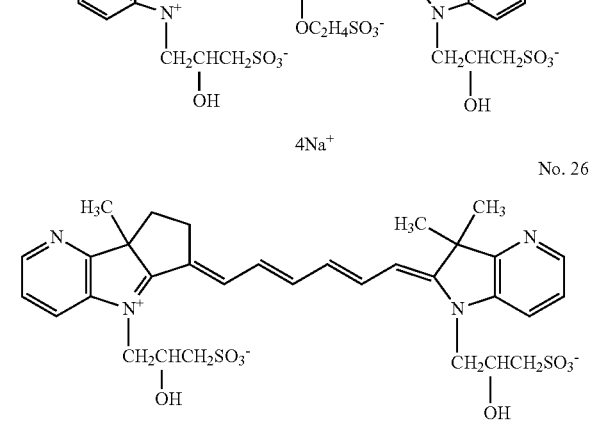
Na+
No. 27
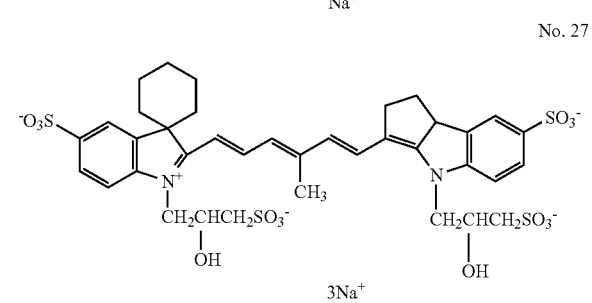
3Na+

-continued
No. 28
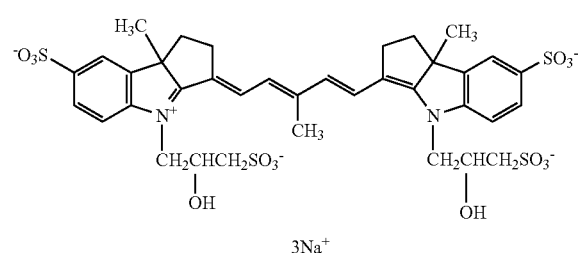
No. 29
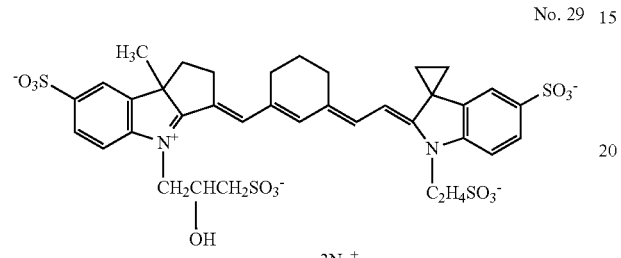
No. 30
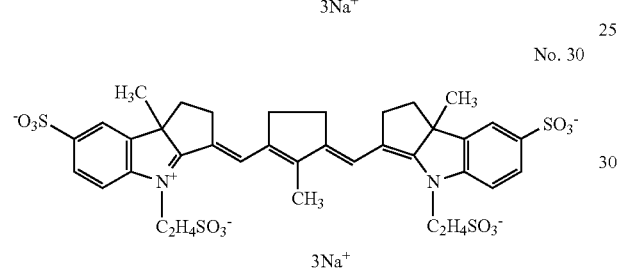
No. 31
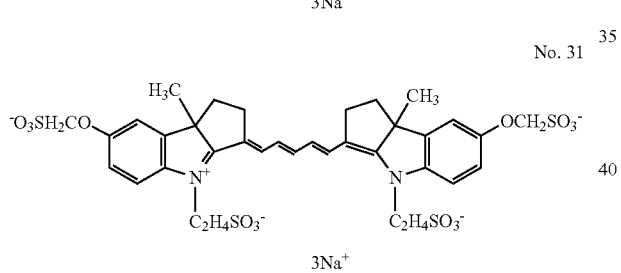
No. 32
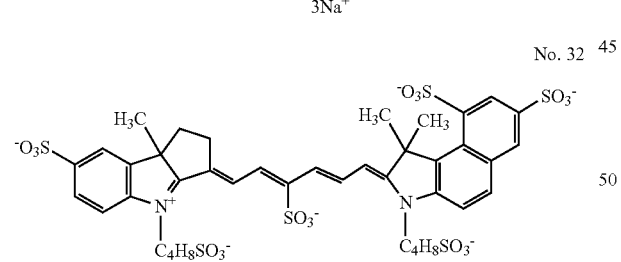
No. 33
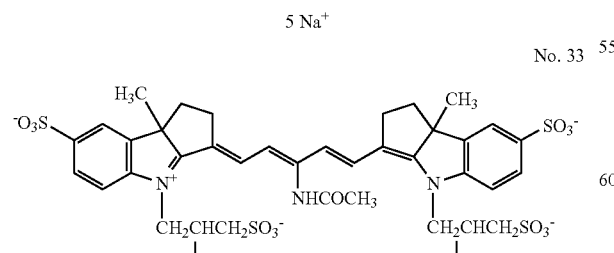
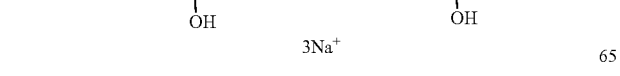
-continued
No. 34
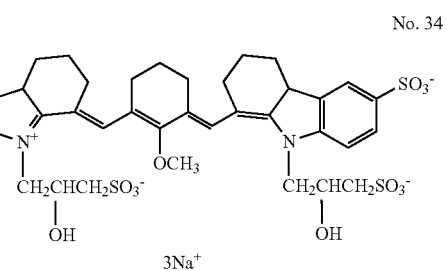
No. 35
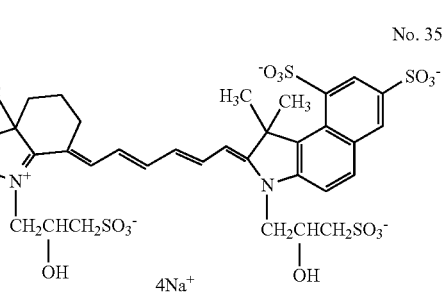
No. 36
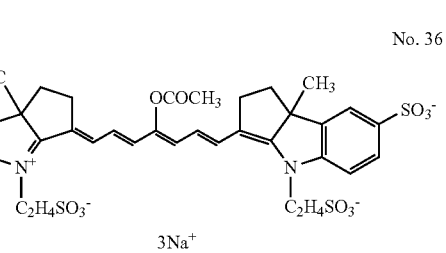
No. 37
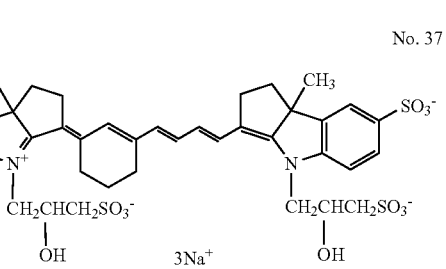
No. 38
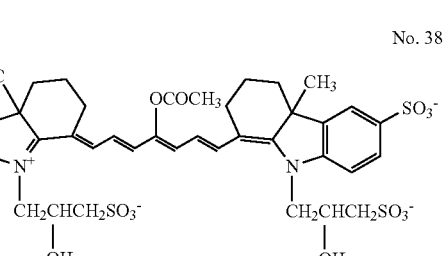
No. 39
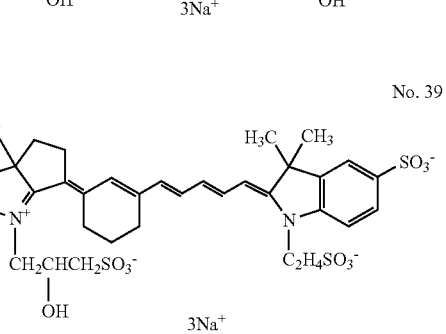

SYNTHESIS EXAMPLE

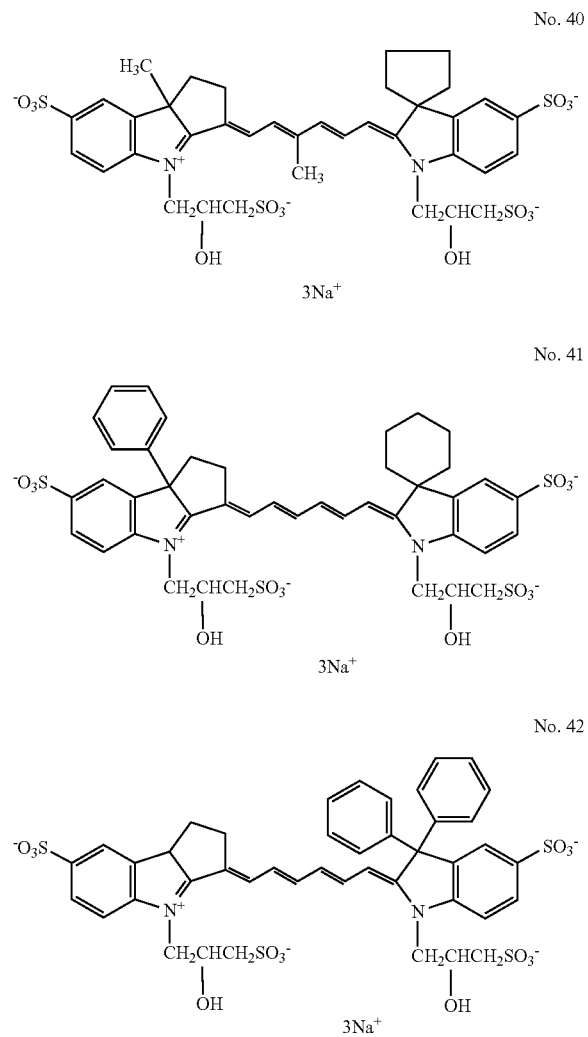

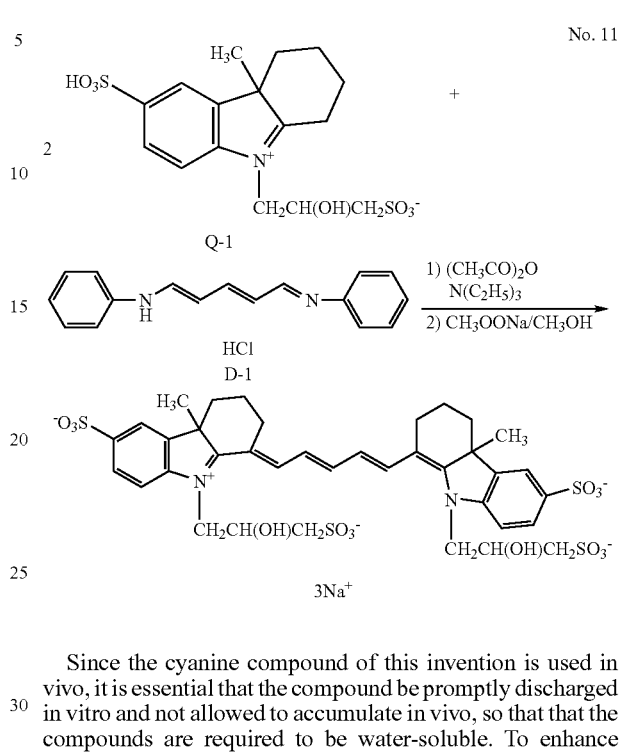

The cyanine compounds relating to this invention can be synthesized in accordance with preparation methods of commonly known cyanine compounds, described in F. M. Hamer in The Cyanine Dyes and Related Compounds, John Wiley and Sons, New York, 1964; Cytometry, 10 (1989) 3-10; Cytomery, 11 (1990) 418-430; Cytometry, 12 (1990) 723-730; Biocojugate Chem. 4 (1993) 105-111; Anal. Biochem. 217 (1994) 197-204; Tetrahedron 45 (1989) 4845-4866; European Patent Nos. 0591820A1 and 05580145A1; JP-A Nos. 4-147131, 2003-48891, 2003-64063 and 2003-261464 (in which the term, JP-A refers to unexamined Japanese Patent Application Publication) and can also be synthesized from commercially available cyanine compounds through appropriate methods known to the art. Specifically, the cyanine compounds can be synthesized through the reaction a dianil compound with a heterocyclic quaternary ammonium salt.

The cyanine compound of formula (I), for example, compound No. 11 can be synthesized by the method shown in the following scheme. Other compounds can also be synthesized in a similar manner.

Since the cyanine compound of this invention is used in vivo, it is essential that the compound be promptly discharged in vitro and not allowed to accumulate in vivo, so that that the compounds are required to be water-soluble. To enhance water-solubility of the cyanine compound, it is preferably a salt of an anionic carboxylic acid or sulfonic acid. In the cyanine compound of this invention, introduction of three sulfonic acid groups has resulted in markedly improved water-solubility. To achieve superior water-solubility are desired at least three sulfonic acid groups, and more preferably at least four sulfonic acid groups. However, to enable easier synthesis of this cyanine compound, ten or less (preferably 8 or less) sulfonic acid groups are desirable.

Water-solubility of these cyanine compounds can be estimated by the measurement of a partition coefficient for each of the compounds, for example, by measuring the partition coefficient in a two-phase system of water and an aliphatic alcohol such as butanol. In a cyanine compound which has introduced at least three sulfonic acid groups, the partition coefficient of n-butanol/water, log Po/w is −1.00 or less. Whether the compound is water-soluble in vivo or not can be judged in a manner that a cyanine compound is dissolved in a physiological sodium chloride solution and the presence/absence of precipitation or deposition is observed at 36° C. with the elapse of time.

A salt allowable to be dosed in vivo may be any one which is capable of forming a nontoxic salt with the compound (I). Examples thereof include alkali metal salts such as a sodium salt or potassium salt; alkaline earth metal salts such as a magnesium salt or calcium salt; and salts of amino acids such as tryptophan, methionine, phenylalanine, lysine, leucine, isoleucine, valine, threonine and arginine. The cyanine compound preferably is a sodium salt of low toxicity.

Near-infrared Fluorescent Contrast Medium

The near-infrared fluorescent contrast medium of this invention is comprised of the foregoing cyanine compounds. The cyanine compounds of this invention exhibit relatively low toxicity and improved water-solubility and radiate fluorescence in the near-infrared region, so it is capable of being transmitted through organic tissue so that a contrast medium containing the said compound enables noninvasive imaging of tumors and/or blood vessels.

The near-infrared fluorescent contrast medium can be prepared by dissolving the cyanine compound of this invention in a solvent such as distilled water for injection, a normal saline solution or Ringer solution. Further, various auxiliary agents based on pharmaceutical techniques, as other ingredients, may be dissolved into the near-infrared fluorescent contrast medium. Specific examples thereof include various kinds of physiologically allowable additives such a buffering agent, an electrolyte and a chelating agent, and appropriately, a osmotic pressure controlling agent, a stabilizer, a viscosity controlling agent, an antioxidant such as α-tocopherol and a preservative such as methyl paraoxybenzoate.

Various buffering agents include a water-soluble amine type buffering agent, a phosphoric acid buffer solution and a citric acid buffer solution. Chelating agents include pharmaceutically allowable EDTA, EDTANa$_2$-Ca (edetic acid disodium calcium salt) and hexametaphosphoric acid.

To obtain an isotonic solution or suspension, a contrast medium is dissolved or dispersed in a medium at a concentration providing isotonic solution. To form an isotonic solution, other nontoxic water-soluble materials, for example, salts such as sodium chloride or saccharides such as mannitol, glucose, sugar or sorbitol may be added to the aqueous medium.

The near-infrared fluorescent contrast medium of this invention can be dosed to the body by means of injection, pouring, spraying or coating onto the inside of the blood vessels (veins and arteries), oral, abdomen, hypodermic or endodermic portion, vesica or bronchus. The amount of the fluorescent contrast medium to be dosed is not specifically limited as long as it is an amount sufficient to detect the site to be finally examined and can optimally be varied depending on the kind of the used cyanine compound emitting near-infrared fluorescence, the age or body size of the objective to be dosed and the objective organ. Specifically, the cyanine compound is dosed usually in an amount of 0.1 to 100 mg/kg (body weight), and preferably 0.5 to 20 mg/kg (body weight).

The near-infrared contrast medium of this invention can also be suitably used as a contrast medium for animals, for which the dose form, dose passage and dose amount are appropriately chosen in accordance with the body weight or conditions of the objective animal.

The near-infrared contrast medium exhibits characteristics that it accumulates on the tumor tissue when exceeding a given concentration and it is easily discharged in vitro at a concentration less than a prescribed value. Employing such characteristics, the near-infrared contrast medium is usable as a fluorescent contrast medium feasible to perform selective, specific imaging of the tumor tissue. Further, when injected into a blood vessel, the compound of this invention is not easily diffused to the outside of the blood vessel, tends to be retained within the blood vessel and is therefore usable as a contrast medium for blood vessels.

One feature of the fluorescence imaging method of this invention concerns the use of the foregoing contrast medium. The measurement can be conducted by methods known to the art and optimal conditions such as the exciting wavelength and the fluorescence wavelength to be detected are suitably determined based on the kind of cyanine compound to be dosed and the object to be dosed to achieve the highest resolution. The time from dosing the fluorescent contrast medium to the measurement subject to the start of the measurement using the fluorescent imaging method according to this invention, depending on the kind of contrast medium to be dosed and the dosed subject, is preferable to choose a passing time of 10 min. to 6 hr. after dose for the purpose of imaging of a tumor or cancer. When the passing time is too short, fluorescence is scattered overall and it becomes difficult to discriminate the objective region from the other one, and when the passing time is exceedingly long, the contrast medium is discharged in vitro. For the purpose of angiography, it is preferred to conduct the measurement within the passing time from immediately after dosage to one hr.

After dosing the measurement subject with the fluorescent contrast medium, the measurement subject is irradiated with exciting light and fluorescence emitted from the fluorescent contrast medium (cyanine compound) excited by the exciting light is detected by a fluorescence detector. The exciting wavelength, depending on the used cyanine compound, is not specifically limited as long as the compound of this invention efficiently emits fluorescence but near-infrared rays exhibiting superior transmissivity in vivo are preferred. Excitation is usually performed with near-infrared rays of 600 to 1000 nm (preferably 700 to 850 nm) and the resulting fluorescence is detected by a high-sensitive fluorescence detector. There are employed, as an exciting light source, various laser light sources such as an ion laser, a dye laser, a semiconductor laser, and conventional light sources such as a halogen light source and xenon light source. There may also be used various types of optical filters to obtain an optimal wavelength. Similarly, the detection sensitivity of fluorescence can be enhanced using various kinds of optical filters capable of selecting only fluorescence emitted from the fluorescent contrast medium.

EXAMPLES

The present invention will be further described based on examples but the invention is by no means limited to these examples.

Example 1

Synthesis of Compound (11)

To 4.0 g of heterocyclic quaternary salt compound Q-1 synthesized with reference to Tetrahedron 27, page 5631-5639, 1971 were added 20 ml of acetic acid, 3 g of triethylamine, 1.5 g of dianil compound D-1 and 3 g of acetic anhydride and stirred at room temperature for 6 hrs. The reaction solution was filtered to remove impurities and the filtrate was concentrated by distillation under reduced pressure at room temperature. To the concentrated filtrate was added 15 ml methanol solution of 2 g of sodium acetate and stirred at room temperature for 1 hr, thereafter, formed crystals were filtered off and washed with a small amount of methanol. The thus obtained 3.2 g coarse crystals were dissolved in 15 ml of water and after adding 1 g of sodium acetate thereto, 30 ml of methanol was further added and stirred for 1 hr. The formed crystals were filtered off, washed with a small amount of methanol and dried to obtain 2.4 g of the compound (11). Compound (11) exhibited an absorption maximum at 792 nm (in methanol) with a molar extinction coefficient of 257,000 (in methanol).

Synthesis Scheme:

No. 11

[Chemical structure showing compound 2 with HO3S, H3C, and CH2CH(OH)CH2SO3- groups attached to a bicyclic indole-type structure with N+]

+

Q-1

[Chemical structure D-1: diphenyl compound with HCl]

1) (CH3CO)2O
   N(C2H5)3
2) CH3OONa/CH3OH
→

[Chemical structure of final product: symmetric bis-indole cyanine dye with -O3S, H3C, CH3, SO3- groups and CH2CH(OH)CH2SO3- substituents on both nitrogens]

3Na+

Example 2

Exemplified compound 11 of formula (I) was prepared similarly to Example 1.

Example 3

Exemplified compound 4 of formula (I) was prepared similarly to Example 1.

Example 4

Exemplified compound 5 of formula (I) was prepared similarly to Example 1.

Example 5

Exemplified compound 6 of formula (I) was prepared similarly to Example 1.

Example 6

Exemplified compound 12 of formula (I) was prepared similarly to Example 1.

Example 7

Exemplified compound 20 of formula (I) was prepared similarly to Example 1.

Example 8

Exemplified compound 32 of formula (I) was prepared similarly to Example 1.

Example 9

Exemplified compound 37 of formula (I) was prepared similarly to Example 1.

Example 10

Exemplified compound 39 of formula (I) was prepared similarly to Example 1.

Example 11

Water-Solubility Test of Compound

In 1 ml of normal saline solution of an official grade was dissolved 0.5 mg of a dye (i.e., the cyanine compound to be tested) to make a solution. The solution was allowed to stand at 42° C. over a period of 1 week to confirm precipitation or the presence of deposits and evaluated based on the following criteria:
A: neither precipitation nor deposit was observed;
B: a slight haze was observed but disappeared by stirring;
C: a haze was observed and did not disappeared by stirring;
D: precipitation and deposits were observed.

Preparation of Model Mouse of Breast Cancer

Model mice having breast cancer were prepared by dosing a carcinogene, 7,12-dimethylbenz[a]anthracene (DMBA) to an acceleratedly aged mice, SAMP6/Ta type mouse as one system of a so-called SAM type to cause breast cancer. Carcinogenesis was carried out in accordance with the description of JP-A No. 2003-033125. To each of 20 SAMP6/Ta type mice, DMBA was dosed in an amount of 0.5 mg/mouse·week, a total of six times. Solid high-protein, high-calorie CA-1 (available from CLEA Japan Inc.) was fed to the mice. After completion of the 6th dose of the carcinogenic substance, the dosage was stopped until the 20th month calculated from the 1st month. Breast cancer and lung metastasis were examined in the manner of pathologic histology. Mice exhibiting breast cancer (at breast cancer incidence of 75%) were used in the following fluorescent contrast imaging test.

Imaging Test

A segment (2 mm×2 mm square) of tumor tissue of the foregoing breast cancer mouse was implanted below the skin of the breast in the left chest of a BALB/c nude mouse (5 weeks old, CLEA Japan Inc.). After 10 days, when the tumor has grown up to a diameter of approximately 5 mm, the foregoing mice were subjected to the fluorescent contrast imaging test. A titanium/sapphire laser was used as an exciting light source. The test mice in a darkened box were uniformly exposed to laser light using a ring-type light guide (available from Sumita Optical Glass Inc.) so that the dispersion of exposure fell within 2%. The irradiation output was adjusted so as to be about 38 $\mu W/cm^2$ near the skin surface of the mice. Fluorescence was emitted by excitation at the absorption peak wavelength of the respective compounds and fluorescent radiation from the mice was subjected to detection and imaging by using a CCD camera (C4880, produced by Hamamatsu Photonics K.K.) together with a filter to cut reflection of incident light at the shorter wavelength side. The exposure time was adjusted in accordance with the fluorescence intensity of the respective compounds. As to the tumor portion, the image obtained by attaching a marker onto the skin surface and observing it under white light was superposed onto the image obtained by removing the marker, followed by exposure to a laser light in the dark and evaluation was made with respect to fluorescence emitted from the tumor portion.

Each of the test compounds shown in Table 1 was dissolved in a normal saline solution (at 0.5 mg/ml) and dosed to the mice through a lactiferous duct and an adenoid lobe. The dose was 3 mg/kg for the respective test compounds. The mice were anesthetized with diethyl ether at the time of 30 min., 12 hr. and 24 hr. after the dosage and the whole body of the respective mice was subjected to fluorescent imaging and fluorescence of the tumor portion was evaluated based on the following criteria:

A: fluorescence was clearly observed in the tumor portion;
  B: fluorescence was also observed in the normal portion but the tumor portion was discernible;
  C: the normal portion and the tumor portion emitted slight fluorescence but the tumor portion was barely discernible;
  D: slight fluorescence was emitted overall and the tumor portion was not discernible from the normal portion;
  E: no fluorescence was observed.

Discharge in vitro of a cyanine compound of contrast medium material was determined by fitting a urethra with a catheter and summing up the discharge over one week after the dosage, and represented by a relative value, based on the amount in vivo of the cyanine compound after the dosage thereof being 100. The discharge of a cyanine compound was determined using liquid chromatograph 2010 (available from Shimazu Corporation).

Results are shown in Table 1. As a comparative contrast medium were used the following indoaniline green (denoted as C-1) and exemplified compound No. 29 (denoted as C-2) described in JP-A No. 2000-95758.

What is claimed is:

1. A near-infrared fluorescent contrast medium comprising a cyanine compound represented by the following formula (I):

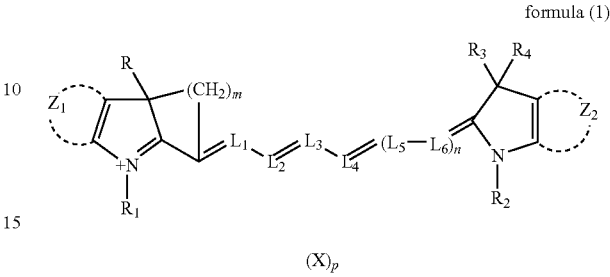

formula (1)

wherein R is a hydrogen atom, a lower alkyl group or an aromatic group; $R_1$ and $R_2$ are each an aliphatic group containing a water-solubilizing group; $R_3$ and $R_4$ are each a lower alkyl group or an aromatic group, provided that $R_3$ and $R_4$ may combine with each other to form a carbocyclic ring; $L_1$ to $L_6$ are each a methine group, provided that when n is 1 or 2, $L_6$ combine with $R_3$ or $R_4$ to form a carbocyclic ring and when n is 0, $L_4$ may combine with $R_3$ or $R_4$ to form a carbocyclic ring; $Z_1$ and $Z_2$ are each a nonmetallic atom group necessary to form a 6-membered ring; X is a counter ion necessary to neutralize a charge of the molecule; p is the number of X necessary to neutralize a charge of the molecule; m is an integer of 2 to 4; and n is an integer of 0 to 2.

2. The contrast medium of claim 1, wherein the water-solubilizing group is a sulfonic acid group.

TABLE 1

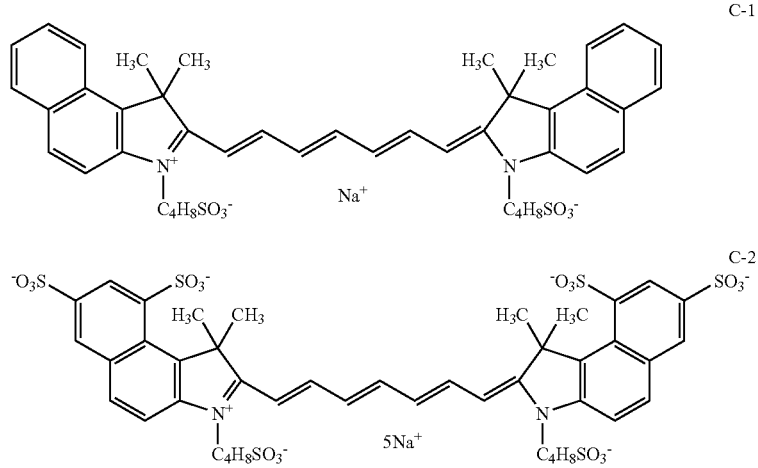

| Example No. | Compound | Water-Solubility | Contrast Imaging | Discharge in vitro (%) |
|---|---|---|---|---|
| Comp. Example 1 | C-1 | C | C | 99.0 |
| Comp. Example 2 | C-2 | B | B | 97.0 |
| Example 2 | 2 | A | A | 99.0 |
| Example 3 | 4 | A | A | 99.0 |
| Example 4 | 5 | A | A | 99.0 |
| Example 5 | 6 | A | A | 99.0 |
| Example 6 | 12 | A | A | 99.0 |
| Example 7 | 20 | A | A | 99.0 |
| Example 8 | 32 | A | A | 99.0 |
| Example 9 | 37 | A | A | 99.0 |
| Example 10 | 39 | A | A | 99.0 |

3. The contrast medium of claim 1, wherein the cyanine compound is represented by the following formula (II) and contains at least two water-solubilizing groups in the molecule:

formula (II)

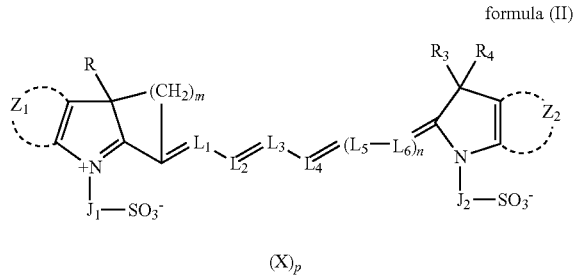

$(X)_p$ wherein $J_1$ and $J_2$ are each an alkylene group having 1 to 5 carbon atoms; R, $R_3$, $R_4$, $L_1$ to L6, $Z_1$, $Z_2$, m, n, p and X are each the same as defined in formula (I).

4. The contrast medium of claim 3, wherein the cyanine compound contains at least four sulfonic acid groups in the molecule.

5. The contrast medium of claim 1, wherein the cyanine compound is represented by the following formula (III):

formula (III)

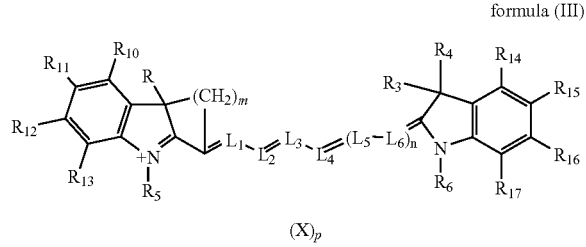

$(X)_p$ wherein $R_5$ and $R_6$ are each a sulfoalkyl group having 3 to 5 carbon atoms and containing a water-solubilizing group; R, $R_3$, $R_4$, $L_1$ to $L_6$, m, n, p and X are each the same as defined in formula (I); $R_{10}$ to $R_{17}$ are each a hydrogen atom or a substituent having a π value of less than 0.3.

6. The contrast medium of claim 5, wherein the π value is represented by the following formula: π=log P(PhX)-log P(PhH) wherein P is a partition coefficient with respect to octanol/water; log P(PhX) is a log P value of a benzene containing substituent X; log P(PhH) is a log P value of benzene.

7. A method of imaging a targeted portion of a living body comprising the steps of introducing a near-infrared fluorescent contrast medium into the living body; exposing the living body to exciting light; detecting a near-infrared fluorescence emitted from the near-infrared fluorescent contrast medium; and forming the image from the detected near infrared fluorescent emission wherein the near-infrared fluorescent contrast medium comprises a cyanine compound represented by the following formula (I):

formula (I)

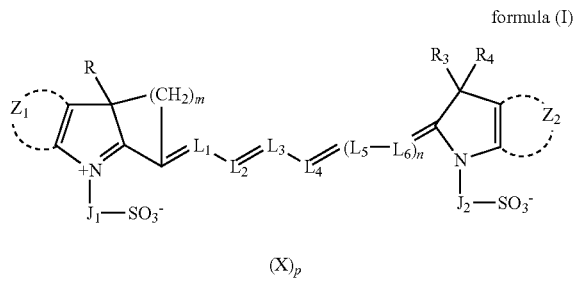

$(X)_p$ wherein R is a hydrogen atom, a lower alkyl group or an aromatic group; $R_1$ and $R_2$ are each an aliphatic group containing a water-solubilizing group; $R_3$ and $R_4$ are each a lower alkyl group or an aromatic group, provided that $R_3$ and $R_4$ may combine with each other to from a carbocyclic ring; $L_1$ to $L_6$ are each a methine group, provided that when n is 1 or 2, $L_6$ combine with $R_3$ or $R_4$ to from a carbocyclic ring and when n is 0, $L_4$ may combine with $R_3$ or $R_4$ to from a carbocyclic ring; $Z_1$ and $Z_2$ are each a nonmetallic atom group necessary to from a 6-membered ring; X is a counter ion necessary to neutralize a charge of the molecule; p is the number of X necessary to neutralize a charge of the molecule; m is an integer of 2 to 4; and n is an integer of 0 to 2.

8. The method of claim 7, wherein the water-solubilizing group is a sulfonic acid group.

9. The method of claim 7, wherein the cyanine compound is represented by the following formula (II) and contains at least two water-solubilizing groups in the molecule:

formula (II)

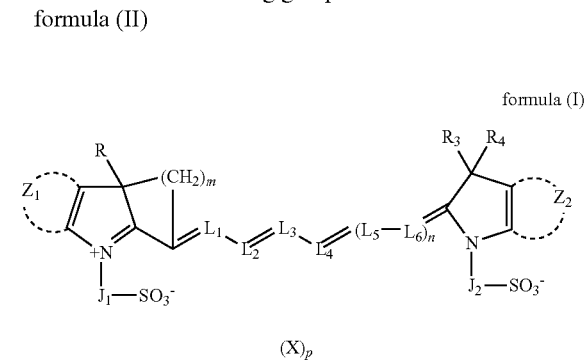

$(X)_p$ wherein $J_1$ and $J_2$ are each an alkylene group having 1 to 5 carbon atoms; R, $R_3$, $R_4$, $L_1$ to $L_6$, $Z_1$, $Z_2$, m, n, p and X are each the same as defined in formula (I).

10. The method of claim 9, wherein the cyanine compound contains at least four sulfonic acid groups in the molecule.

11. The method of claim 7, wherein the cyanine compound is represented by the following formula (III):

formula (III)

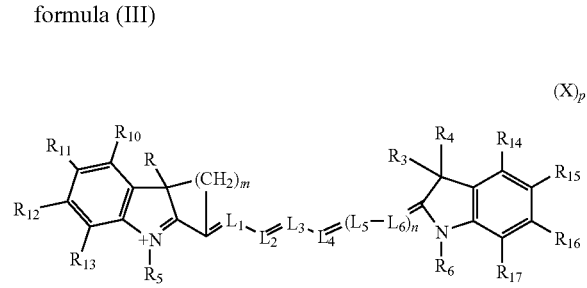

wherein $R_5$ and $R_6$ are each a sulfoalkyl group having 3 to 5 carbon atoms and containing a water-solubilizing group; R, $R_3$, $R_4$, $L_1$ to $L_6$, m, n, p and X are each the same as defined in formula (I); $R_{10}$ to $R_{17}$ are each a hydrogen atom or a substituent having a π value of less than 0.3.

12. The method of claim 11, wherein the π value is represented by the following formula: π=log P(PhX)-log P(PhH) wherein P is a partition coefficient with respect to octanol/water; log P(PhX) is a log P value of a benzene containing substituent X; log P(PhH) is a log P value of benzene.

* * * * *